United States Patent

Eberlein et al.

[11] 4,038,407
[45] July 26, 1977

[54] BENZISOTHIAZOLINE-1,1-DIOXIDE DERIVATIVES, COMPOSITIONS AND METHODS

[75] Inventors: Wolfgang Eberlein; Eberhard Kutter, both of Biberach an der Riss; Joachim Heider, Warthausen; Volkhard Austel, Biberach an der Riss; Rüdolf Kadatz, Biberach an der Riss; Willi Diederen, Biberach an der Riss, all of Germany; Walter Kobinger; Christian Lillie, both of Vienna, Austria; Jürgen Dämmgen, Warthausen, Germany

[73] Assignee: Boehringer Ingelheim GmbH, Ingelheim am Rhein, Germany

[21] Appl. No.: 660,841

[22] Filed: Feb. 24, 1976

[30] Foreign Application Priority Data

Mar. 6, 1975 Germany .............................. 2509797
Dec. 23, 1975 Germany .............................. 2558274

[51] Int. Cl.² .................... A61K 31/425; C07D 91/12
[52] U.S. Cl. ..................... 424/270; 260/305; 260/304 A; 260/325 PH; 424/274
[58] Field of Search ............... 260/304 A; 424/270

[56] References Cited

U.S. PATENT DOCUMENTS

| | | | |
|---|---|---|---|
| 3,164,602 | 1/1965 | Childress et al. | 424/270 |
| 3,227,715 | 1/1966 | Bub | 260/304 A |
| 3,657,263 | 4/1972 | Vitali et al. | 260/304 A |
| 3,890,340 | 6/1975 | Singerman | 260/304 A |

*Primary Examiner*—Norman A. Drezin
*Attorney, Agent, or Firm*—Hammond & Littell

[57] ABSTRACT

Compounds of the formula

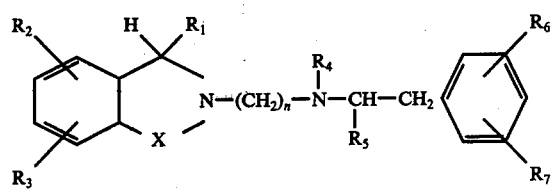

wherein
$R_1$ is hydrogen, lower alkyl or phenyl,
$R_2$ is hydrogen, chlorine or methoxy,
$R_3$ is hydrogen or methoxy,
$R_2$ and $R_3$, together with each other, are methylenedioxy or ethylenedioxy,
$R_4$ and $R_5$ are each hydrogen or lower alkyl
$R_6$ is hydrogen or lower alkoxy,
$R_7$ is lower alkoxy,
$R_6$ and $R_7$, together with each other, are methylenedioxy or ethylenedioxy,
X is carbonyl or sulfonyl, and
n is 2 or 3, and non-toxic, pharmacologically acceptable acid addition salts thereof; the compounds as well as the salts are useful for slowing the heart rate.

4 Claims, No Drawings

BENZISOTHIAZOLINE-1,1-DIOXIDE DERIVATIVES, COMPOSITIONS AND METHODS

This invention relates to novel substituted aralkylamines and non-toxic acid addition salts thereof, as well as to methods of preparing these compounds.

More particularly, the present invention relates to a novel class of aralkylamines represented by the formula

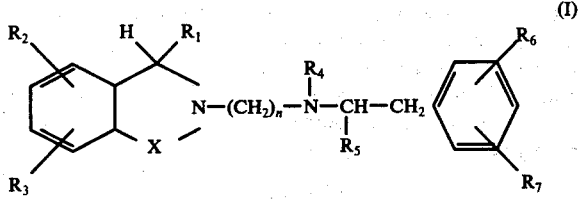

wherein
- $R_1$ is hydrogen, lower alkyl or phenyl,
- $R_2$ is hydrogen, chlorine or methoxy,
- $R_3$ is hydrogen or methoxy,
- $R_2$ and $R_3$, together with each other are methylenedioxy or ethylenedioxy,
- $R_4$ and $R_5$ are each hydrogen or lower alkyl,
- $R_6$ is hydrogen or lower alkoxy,
- $R_7$ is lower alkoxy,
- $R_6$ and $R_7$, together with each other, are methylenedioxy or ethylenedioxy,
- X is carbonyl or sulfonyl, and
- n is 2 or 3, and non-toxic, pharmacologically acceptable acid addition salts thereof.

The term "lower alkyl," as used herein to define $R_1$, $R_4$ and $R_5$ is intended to designate alkyl of 1 to about 7 carbon atoms, but preferred embodiments thereof are methyl, ethyl, propyl, or isopropyl.

Similarly, the term "lower alkoxy," as used herein to define $R_6$ and $R_7$ is intended to designate alkoxy of 1 to about 7 carbon atoms, but preferred embodiments thereof are methoxy, ethoxy, propoxy or isopropoxy.

The compounds embraced by formula I above may be prepared by the following methods:

Method A

By reacting a compound of the formula

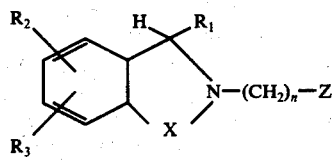

wherein
- $R_1$, $R_2$, $R_3$, X and n have the same meanings as in formula I, and
- Z is a leaving group, such as chlorine, bromine, iodine, alkylsulfonyloxy or arylsulfonyloxy, with a phenylethylamine of the formula

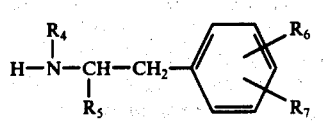

wherein $R_4$, $R_5$, $R_6$ and $R_7$ have the same meanings as in formula I.

The reaction is advantageously carried out in the presence of a solvent, such as methanol, ether, tetrahydrofuran, methylformamide, dimethylformamide, dimethylsulfoxide or benzene, and at a temperature between −50° and 250° C, depending on the reactivity of the leaving group Z. The presence of an acid binding agent, for example, an alkali metal alcoholate, an alkali metal hydroxide or a tertiary organic base such as triethylamine or pyridine, or of a reaction accelerator, such as potassium iodide, is of advantage.

Method B

For the preparation of a compound of the formula I, wherein $R_1$ is hydrogen and X is carbonyl, by reducing a compound of the formula

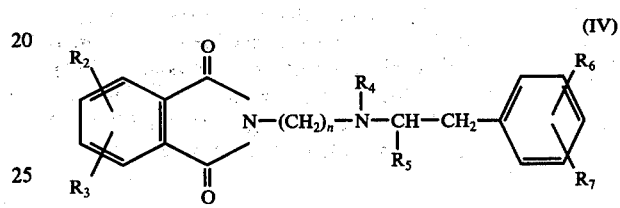

wherein $R_2$, $R_3$, $R_4$, $R_5$, $R_6$, $R_7$ and n have the same meanings as in formula I.

The reduction is preferably carried out in the presence of a solvent, such as glacial acetic acid, water or ethanol, and advantageously with nascent hydrogen, generated, for example, by zinc-glacial acetic acid, tin-hydrochloric acid or tin(II)chloride-hydrochloric acid, or with catalytically activated hydrogen, at temperatures between 0° and 250° C, preferably, however, between 50° and 100° C.

In those instances where the end product of method A or B is a compound of the formula I wherein $R_4$ is hydrogen, that compound may, if desired, be subsequently alkylated, for example by reacting it with a corresponding alkyl halide or dialkyl sulfate; or it may be methylated by reaction with formaldehyde/formic acid.

The compounds embraced by formula I are organic bases and therefore form addition salts with inorganic or organic acids. Examples of non-toxic, pharmacologically acceptable acid addition salts are those formed with hydrochloric acid, phosphoric acid, hydrobromic acid, sulfuric acid, lactic acid, tartaric acid, maleic acid, 8-chlorotheophylline or the like.

The starting compounds of the fomrulas II, III and IV are either known compounds or may be prepared by known methods.

The following examples illustrate the present invention and will enable others skilled in the art to understand it more completely. It should be understood, however, that the invention is not limited solely to the particular examples given below.

EXAMPLE 1

2N-(3-[α-(3,4-Dimethoxy)-phenylethyl-methylamino]-propyl)-phthalimidine hyrochloride by method B.

a. 5.04 gm (0.02 mol) of 1-[2-(3,4-dimethoxy-phenethyl)-methyl-amino]-3-amino-propane and 2.06 gm (0.02 mol) of phthalic acid anhydride were dissolved in 100 ml of glacial acetic acid, and the solution was refluxed for 4 hours. Subsequently, the reaction mixture was evaporated in vacuo, the residue was taken up in chloroform, and the chloroform solution was successively washed with a saturated aqueous sodium bicarbonate solution and water. After drying over sodium sulfate, the solvent was distilled off, leaving 6.1 gm (79.8% of theory) of amorphous 2N-(3-[α-(3,4-Dimethoxy)-phenethylmethylamino]-propyl)-phthalimide, $R_f$-value: 0.4 (benzene/acetone = 1/1).

b. A solution of 6.1 gm (159 millimols) of 2N-(3-[α-(3,4-dimethoxy-phenethyl)-methylamino]-propyl)-phthalimide in 80 ml of glacial acetic acid was admixed with 10 g of zinc dust, and the mixture was refluxed for three hours. Thereafter, the reaction mixture was filtered while still hot to separate the residual zinc dust, and the filtrate was evaporated in vacuo. The residue was dissolved in chloroform, and the resulting solution was extracted with a saturated aqueous bicarbonate solution and then with water, dried over sodium sulfate and evaporated. The residue was purified by chromatography on silicagel (chloroform/methanol = 19/1), precipitated from ethereal hydrochloric acid and digested with ethyl acetate, yielding 2.25 gm (35% of theory) of the hydrochloride of the formula

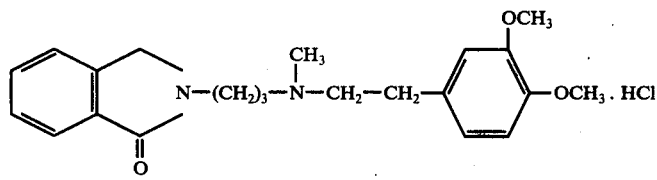

which had a melting point of 146°-148° C.

EXAMPLE 2 a. 5,6-Dimethoxy-2N-(3-[α-(3,4-dimethoxy-phenethyl)-methylamino]-propyl)-phthalimide was prepared analogous to Example 1(a) by condensation of 4,5-dimethoxy-phthalic acid anhydride with 1-[2-(3,4-dimethoxy-phenyl)-ethyl-methylamino]-3-amino-propane in glacial acetic acid. M.p.: 91°-93° C.

b. 5,6-Dimethoxy-2N-(3-[α-(3,4-dimethoxy)-phenylethyl-methylamino]-propyl)-phthalimidine hydrochloride was prepared analogous to Example 1(b) by reduction of 5,6-dimethoxy-2N-(3-[α-(3,4-dimethoxy)-phenethyl)-methylamino]-propyl)-phthalimide with zinc dust in glacial acetic acid. M.p.: 170°-172° C.

EXAMPLE 3 a. 5,6-Dimethoxy-2N-(3-[α-(3,4-dimethoxy)-phenylethylamino]-propyl)-phthalimide was prepared analogous to Example 1(a) by condensation of 4,5-dimethoxy-phthalic acid anhydride with 1-[2-(3,4-dimethoxy-phenyl)-ethylamino]-3-amino-propane in glacial acetic acid. $R_f$ value (chloroform/methanol = 9/1): 0.25.

b. 5,6-Dimethoxy-2N-(3-[α-(3,4-dimethoxy)-phenylethylamino]-propyl)-phthalimidine hydrochloride was prepared analogous to example 1(b) by reduction of 5,6-dimethoxy-2N-(3-[α-(3,4-dimethoxy)-phenylethylamino]propyl)-phthalimide with zinc dust in glacial acetic acid. M.p.: 207°-209° C.

EXAMPLE 4

5,6-Dimethoxy-2N-(3-[α-(3,4-dimethoxy)-phenylethylmethylamino]-propyl)-phthalimidine hydrochloride 5 gm (12.1 mols) of the end product obtained in Example 3(b) were heated up to 100° C in a mixture of 1.38 gm (30 millimols) of formic acid and 1.5 gm (20 millimols) of formalin for 1 hour. After cooling, the reaction solution was made alkaline by addition of 2 N sodium hydroxide, extracted with chloroform, and the chloroform phase was washed with water, dried and evaporated in vacuo. The residue was purified by chromatography on silicagel (chloroform/methanol = 45/1), the combined main fractions were evaporated, and the base was precipitated as the hydrochloride from ethereal hydrochloric acid. M.p.: 170°-172° C.

EXAMPLE 5

5,6-Dimethoxy-2N-(3-[α-(3,4-dimethoxy)-phenylethyl-n-propylamino]-propyl)-phthalimidine hydrochloride A solution of 25 gm (5.5 millimols) of 5,6-dimethoxy-2N-(3-[α-(3,4-dimethoxy)-phenylethylamino]-propyl)-phthalimidine in 100 ml of acetone was refluxed for 6 hours after addition of 20 ml of 1-bromopropane and 5 gm of potassium carbonate. After cooling, the solid substance was filtered off, and the filtrate was evaporated. The residue was taken up in ether, the insoluble matter was again filtered off, and after evaporation of the filtrate the hydrochloride was precipitated from ethereal hydrochloric acid. M.p.: 120°-122° C (acetone/methanol).

EXAMPLE 6

5,6-Dimethoxy-2N-(3-[α-(3,4-dimethoxy)-phenylethyl-methyl-amino]-ethyl)-phthalimidine hydrochloride by method B 3.81 gm (15 millimols) of N-(2-bromoethyl)-phthalimide were refluxed together with 6 gm of 3,4-dimethoxyphenylethyl-N-methylamine in 40 ml of xylene for 10 hours. The oily residue obtained after evaporation in vacuo was converted into the desired compound analogous to Example 1(b) by reduction with zinc dust in glacial acetic acid without further purification. M.p.: 149°-151° C.

EXAMPLE 7

2N-(3-[α-(3,4-Dimethoxy)-phenylethyl-methylamino]-propyl-3-phenyl-phthalimidine by method A 1.75 gm (5.3 millimols) of N-(3-bromopropyl)-3-phenyl-phthalimidine were refluxed into 2.06 gm (10.6 millimols) of 3,4-dimethoxyphenylethyl-N-methylamine in 30 ml of xylene for 10 hours. After cooling, the mixture was evaporated, and the residue was purified by chromotography on silicagel (chloroform/methyl alcohol = 19/1). The base was obtained as a highly viscous oil. $R_f$-value (chloroform/methanol = 19/1): 0.4.

EXAMPLE 8

3-Phenyl-5-chloro-2N-(3-[α-(3,4-dimethoxy)-phenylethyl-methylamino-propyl]-1,2-benzisothiazoline-1,1-dioxide hydrochloride by method A 3 gm (9.3 millimols) of N-(3-chloropropyl)-3-phenyl-5-chloro-1,2-benzisothiazoline-1,1-dioxide were refluxed together with 3 gm of 3,4-dimethoxy-phenylethyl-N-methylamine and a spatula tipful of potassium iodide in a mixture of 30 ml of dimethylformamide and 5 ml of triethylamine for 5 hours. Subsequently, the reaction mixture was evaporated to dryness, the residue was taken up in chloroform, and the organic phase was washed several times with water. After drying, the solution was evaporated, and the residue was purified by chromatography on silicagel (chloroform/methanol = 40/1). Precipitation of the purified product from ethereal hydrochloric acid yielded the amorphous hydrochloride of the formula

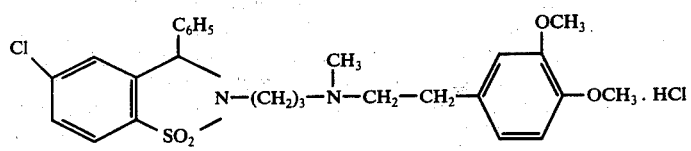

$R_f$-value (chloroform/methanol = 19/1): 0.5.
$C_{27}H_{31}ClN_2O_4S \times HCl$ (551.54) Calculated: C-58.8%; H-5.60%; N-5.10%; S-5.80% Found: C-58.7%; H-5.75%; N-5.20%; S-5.90%

EXAMPLE 9

5,6-Dimethoxy-2N-(3-[α-3,4-dimethoxy)-phenylethylmethylamino]-propyl)-1,2-benzisothiazoline-1,1-dioxide hydrochloride by method A a. 2-Methyl-4,5-dimethoxy-benzene sulfochloride 23.2 gm (0.2 mol) of chlorosulfonic acid were slowly added dropwise to 15.2 gm (0.1 mol) of 3,4-dimethoxy-toluene at about − 10° C, while stirring and cooling. Afterwards, the mixture was allowed to warm to room temperature, and was then stirred until the evolution of hydrogen chloride ceased. The reaction mixture was poured over ice, and the precipitated sulfochloride was extracted with ether. The organic phase was successively washed with sodium bicarbonate solution and water, and then evaporated to dryness in vacuo. A turbid oil was obtained as a residue, which solidified after cooling. $R_f$-value (benzene): 0.5.

b. 2-Methyl-4,5-dimethoxy-benzene sulfonamide 18 gm (0.07 mol) of the compound obtained in step (a) were suspended in 200 ml of concentrated ammonia, and the suspension was stirred at room temperature for 4 hours. Thereafter, the mixture was suction-filtered, the filter cake was washed with water, and the desired sulfonamide was obtained as an amorphous product after drying. $R_f$-value (benzene/acetone = 1/1): 0.6.

c. 5,6-Dimethoxy-1,2-benzisothiazoline-3-one-1,1-dioxide 16 gm (0.08 mol) of 2-methyl-4,5-dimethoxy-benzene sulfonamide were dissolved in 500 ml of an aqueous 5% sodium hydroxide solution, and the solution was heated at its boiling point for 2 hours after addition of 39.6 gm (0.25 mol) of potassium permanganate. After cooling, the reaction mixture was suction-filtered through celite, and the desired product was precipitated by addition of concentrated hydrochloric acid. $R_f$-value (benzene/acetone = 3/1): 0.2–0.4.

d. 5,6-Dimethoxy-1,2-benzisothiazoline-1,1-dioxide 7 gm (288 millimols) of the compound obtained in step (c) were refluxed for 2 hours with 3.3 gm (865 millimols) of lithium aluminum hydride in 400 ml of tetrahydrofuran. After cooling, the excess lithium aluminum hydride was decomposed by addition of ethyl acetate, the mixture was diluted with water, and subsequently 2 N hydrochloric acid was added until the aluminum hydroxide precipitate was dissolved. The reaction solution now extracted with ethyl acetate, and the organic phase was washed with water, dried and evaporated in vacuo. The residue was digested in ether, and the desired compound was suction-filtered off.

e. N-(3-Chloropropyl)-5,6-dimethoxy-1,2-benzisothiazoline-1,1-dioxide 2.4 gm (10.5 millimols) of the compound obtained in step (d) were dissolved in a mixture of 15 ml of an aqueous 2.5% sodium hydroxide solution and 30 ml of ethanol, and the solution was refluxed for 8 hours after addition of 10 ml of 3-bromo-1-chloro-propane. The reaction mixture was thereafter evaporated to half its volume, diluted with water and extracted with chloroform. After drying of the organic phase it was evaporated in vacuo, and the desired product was obtained as a highly viscous oil. $R_f$-value (chloroform/methanol = 19/1: 0.8.

f. 5,6-Dimethoxy-2N-(3-[α-(3,4-dimethoxy)-phenylethylmethylamino]-propyl)-1,2-benzisothiazoline-1,1-dioxide hydrochloride was prepared analogous to Example 8 by reaction of N-(3-chloropropyl)-5,6-dimethoxy-1,2-benzisothiazoline-1,1-dioxide with 3,4-dimethoxyphenylethyl-N-methylamine. M.p.: 196°–198° C (acetone).

EXAMPLE 10

5,6-Methylenedioxy-2N-(3-[α-(3,4-dimethoxy)-phenylethylmethylamino]-propyl)-phthalimidine hydrochloride by method B a. 3.5 gm (18 millimols of 4,5-methylenedioxy-phthalic acid anhydride and 4.5 gm (18 millimols) of 1-[2-(3,4-dimethoxy-phenyl)-ethylmethylamino]-3-amino-propane were refluxed in 100 ml of glacial acetic acid for 2 hours. Subsequently, the reaction mixture was evaporated in vacuo, the residue was taken up in chloroform, and the chloroform solution was successively washed with a saturated aqueous sodium bicarbonate solution and water. After drying over sodium sulfate, the solvent was distilled off, and the desired substance was obtained as an amorphous product. Yield: 4.8 gm (63% of theory); $R_f$-value (chloroform/methanol = : 9/1): 0.6.

b. 5,6-Methylenedioxy-2N-(3-[α-(3,4-dimethoxy)-phenylethyl-methylamino]-propyl)-phthalimidine hydrochloride A solution of 4.8 gm (11 millimols) of 5,6-methylenedioxy-2N-(3-[α-(3,4-dimethoxy)-phenylethyl-methylamino]-propyl)-phthalimide in 40 ml of glacial acetic acid was admixed with 5 gm of zinc dust, and the mixture was refluxed for 2 hours. Afterwards, the residual zinc dust was filtered off from the hot reaction solution, and the filtrate was evaporated in vacuo. The residue was dissolved in chloroform, and the organic phase was extracted first with a saturated aqueous sodium carbonate solution and then with water, dried over sodium sulfate and evaporated. The residue was redissolved in chloroform and the solution was admixed with ethereal hydrochloride, yielding 1.5 gm (30% of theory) of the hydrochloride of the formula

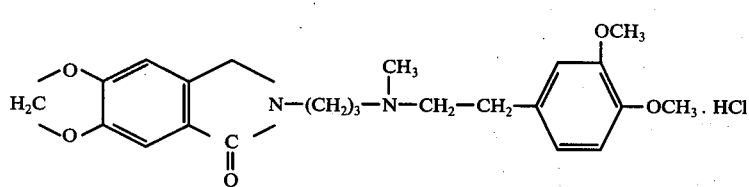

having a melting point of 237°-239° C.
Calculated: C-61.53%; H-6.51%; H-6.24%; Cl-7.90%
Found: C-61.50%; H-6.49%; H-6.24%; Cl-7.85%

EXAMPLE 11 a. 4,5-Ethylenedioxy-2N-(3-[α-(3,4-dimethoxy)-phenylethyl-methylamino]-propyl)-phthalimide was prepared analogous to Example 10(a) by condensation of 4,5-ethylenedioxy-phthalic acid anhydride with 1-[2-(3,4-dimethoxy-phenyl)-ethylmethylamino]-3-aminopropane in glacial acetic acid. $R_f$-value (chloroform/methanol = 9/1): 0.5.

b. 5,6-Ethylenedioxy-2N-(3-[α-(3,4-dimethoxy)-phenylethyl-methylamino]-propyl)-phthalimidine-hydrochloride was prepared analogous to Example 10(b) by reduction of 4,5-ethylenedioxy-2N-(3-[α-(3,4-dimethoxy)-phenylethyl-methylamino]-propyl phthalimide with zinc dust in glacial acetic acid. M.p.: 208°-210° C.
Calculated: C-62.26%; H-6.75%; N-6.05%; Cl-7.66%
Found: C-62.10%; H-6.84%; N-5.90%; Cl-7.67%

EXAMPLE 12 a. 4,5-Methylenedioxy-2N-(3-[α-3,4-methylenedioxy)-phenylethyl-methylamino]-propyl)-phthalimide 2.7 gm (10 millimols) of 4,5-methylenedioxy-N-(3-chloropropyl)-phthalamide and 1.8 gm (10 millimols) of 3,4-methylenedioxy-phenylethyl-N-methylamine were dissolved in 20 ml of chlorobenzene, and the solution was refluxed for 8 hours after addition of 2.8 gm (20 millimols) of pulverized potassium carbonate. Subsequently, the reaction solution was filtered, and the filtrate was evaporated to dryness in vacuo. The residue was purified by chromatography on silicagel (chloroform/methanol = 19/1), and after evaporation of the main fraction 2.1 gm (51% of theory) of the desired compound were obtained. $R_f$-value (chloroform/methanol = 9/1): 0.6.

b. 5,6-Methylenedioxy-2N-(3-[α-(3,4-methylenedioxy)-phenylethyl-methylamino]-propyl)-phthalimidine hydrochloride was prepared analogous to Example 10(b) by reduction of 4,5-methylenedioxy-2N-(3-[α-(3,4-methylenedioxy)-phenylethylmethylamino]-propyl)-phthalimide with zinc dust in glacial acetic acid. M.p.: 206°-208° C.
Calculated: C-61.04%; H-5.82%; N-6.47%; Cl-8.19%
Found: C-61.10%; H-6.07%; N-6.74%; Cl-8.45%

EXAMPLE 13 a. 4,5-Ethylendioxy-2N-(3-[α-(3,4-methylendioxy)-phenylethyl-methylamino]-propyl)-phthalimide was prepared analogous to Example 12(a) by reaction of 4,5-ethylenedioxy-N-(3-chloropropyl)-phthalimide with 3,4-methylenedioxy-phenylethyl-N-methylamine in chlorobenzene in the presence of potassium carbonate. $R_f$-value (chloroform-methanol = 9/1): 0.5.

b. 5,6-Ethylenedioxy-2N-(3-[α-(3,4-methylenedioxy)-phenylethyl-methylamino]-propyl-phthalimidine hydrochloride was prepared analogous to Example 10(b) by reduction of 4,5-ethylenedioxy-2N-(3-[α-(3,4-methylenedioxy)-phenylethylmethylamino]-propyl)-phthalimide with zinc dust in glacial acetic acid. M.p.: 180°-182° C.
Calculated: C-61.81%; H-6.09%; N-6.27%; Cl-7.93%
Found: C-61.70%; H-6.12%; N-6.12%; Cl-7.94%

EXAMPLE 14 a. 4,5-Dimethoxy-2N-(3-[α-(3,4-methylenedioxy)-phenylethyl-methylamino]-propyl)-phthalimide was prepared analogous to Example 12(a) by reaction of 4,5-dimethoxy N-(3-chloropropyl)phthalimide with 3,4-methylenedioxy-phenylethyl-N-methylamine in chlorobenzene in the presence of potassium carbonate. $R_f$-value (chloroform/methanol = 19/1): 0.7.

b. 5,6-Dimethoxy-2N-(3-[α-(3,4-methylenedioxy)-phenylethyl-methylamino]-propyl)-phthalmide hydrochloride was prepared analogous to Example 10(b) by reduction of 4,5-dimethoxy-2N-(3-[α-(3,4-methylenedioxy)-phenylethyl-methylamino]-propyl)phthalimide with zinc dust in glacial acetic acid. M.p.: 235°-237° C.
Calculated: C-61.53%; H-6.51%; N-6.24%; Cl-7.90%
Found: C-61.45%; H-6.63%; N-6.27%; Cl-7.92%

EXAMPLE 15

5,6-Ethylenedioxy-2-(3-[α-(3,4-dimethoxy)-phenylethyl-methylamino]-propyl)-1,2-benzisothiazoline-1,1-dioxide hydrochloride was prepared analogous to Example 12(a) by reaction of N-(3-chloropropyl)-5,6-ethylenedioxy-1,2-benzisothiazoline-1,1-dioxide with 3,4-dimethoxy-phenylethyl-N-methylamine. $R_f$-value (chloroform/methanol = 9/1): 0.6.

EXAMPLE 16

3-Methyl-5,6-dimethoxy-2N-(3-[α-(3,4-dimethoxy)-phenylethylmethylamino]-propyl)-phthalimidine hydrochloride was prepared analogous to Example 12(a) by reaction of 3-methyl-5,6-dimethoxy-N-(3-chloropropyl)-phthalimidine with 3,4-dimethoxyphenylethyl-N-methylamine in chlorobenzene in the presence of potassium carbonate. M.p.: 135°-136° C.
Calculated: C-62.68%; H-7.36%; N-5.85%; Cl-7.40%
Found: C-62.31%; H-7.40%; N-5.80%; Cl-7.12%

EXAMPLE 17 a. 4,5-Dimethoxy-2N-(3-[α-(3,4-dimethoxy)-phenylisopropyl-methylamino]-propyl)-phthalimide was prepared analogous to Example 12(a) by reaction of 4,5-dimethoxy-N-(3-chloropropyl)-phthalimide with 3,4-dimethoxy-phenyl-isopropyl-N-methylamine in chlorobenzene in the presence of potassium carbonate. $R_f$-value (chloroform/methanol = 9/1): 0.9.

b. 5,6-Dimethoxy-2N-(3-[α-(3,4-dimethoxy)-phenylisopropyl-methylamino]-proply)-phthalimidine hydrochloride was prepared analogous to Example 10(b) by reduction of 4,5-dimethoxy-2N-(3-[α-(3,4-dimethoxy)-phenylisopropyl-methylamino]-propyl)-phthalimide with zinc dust in glacial acetic acid. M.p.: 183°–185° C.

Calculated: C-62.68%; H-7.36%; N-5.85%; Cl-7.40%; Found: C-62.50%; H-7.42%; N-5.92%; Cl-7.30%

EXAMPLE 18 a. 4,5-Methylenedioxy-2N-(2-[α-(3,4-dimethoxy)-phenylethyl-methylamino]-ethyl)-phthalimide was prepared analogous to Example 10(a) from 4,5-methylenedioxy-phthalic acid anhydride and 1-[2-(3,4-dimethoxy-phenyl)-ethyl-methylamino]-2-amino-ethane. $R_f$-value (chloroform/methanol = 9:1): 0.55.

b. 5,6-Methylenedioxy-2N-(2-[α-(3,4-dimethoxy)-phenylethyl-methylamino]-ethyl)-phthalimidine-hydrochloride was prepared analogous to Example 10(b) by reduction of 4,5-methylenedioxy-2N-(2-[α-(3,4-dimethoxy)-phenylethyl-methylamino]-ethyl)-phthalimide with zinc dust in glacial acetic acid. $R_f$-value (chloroform/methanol = 9:1): 0.4.

The compounds embraced by formula I and their non-toxic, pharmacologically acceptable acid addition salts have useful pharmacodynamic properties. More particularly, they primarily selectively reduce the heart rate and also exhibit mild hypotensive activity in warm-blooded animals, such as guinea pigs.

The heart rate reducing activity and the acute toxicity of the compounds of this invention were ascertained by the standard pharmacological test methods described below, and the test results for a few representative compounds are given, where A = 5,6-Dimethoxy-2N-(3-[α-(3,4-dimethoxy)-phenylethyl-methylamino]-propyl)-phthalimidine hydrochloride, B = 5,6-Dimethoxy-2-(3-[α-(3,4-dimethoxy)-phenylethyl-methylamino]-propyl)-1,2-benzisothiazoline-1,1-dioxide hydrochloride, C = 5,6-Methylenedioxy-2N-(3-[α-(3,4-methylenedioxy)-phenylethyl-methylamino]-propyl)-phthalimidine hydrochloride, D = 5,6-Dimethoxy-2N-(3-[α-(3,4-methylenedioxy)-phenylethylmethylamino]-propyl)-phthalimidine hydrochloride and E = 5,6-Ethylenedioxy-2N-(3-[α-(3,4-methylenedioxy)-phenylethyl-methylamino]-propyl)-phthalimidine hydrochloride.

1. Activity on heart frequency of anesthetized guinea pigs:

The heart rate of guinea pigs under urethane anesthesia was registered by an electrocardiogram. The test compound was administered intravenously at increasing dosage increments between 0.5 and 20 mg/kg.

The following table shows the results obtained:

TABLE I

| Compound | Dose mg/kg i.v. | n | Percentage change in heart rate |
|---|---|---|---|
| A | 0.5 | 3 | −23.5 |
|   | 1.0 | 3 | −36.1 |
|   | 2.0 | 3 | −47.2 |
|   | 5.0 | 3 | −51.6 |
|   | 10.0 | 3 | −59.1 |
|   | 20.0 | 3 | −67.2 |
| B | 0.5 | 5 | −9.8 |
|   | 1.0 | 5 | −20.0 |
|   | 2.0 | 5 | −27.4 |
|   | 5.0 | 5 | −37.6 |
|   | 10.0 | 5 | −46.9 |
|   | 20.0 | 5 | −53.9 | n = number of animals per dose

2. Effect on heart rate in the isolated auricle of the guinea pig:

The effect on isolated, spontaneously beating auricles of guinea pigs of male and female sex having a body weight between 300 and 400 gm were investigated in an organ bath filled with tyrode solution. The nutritive solution was infused with carbogen (95% of $O_2$ and 5% of $CO_2$) and maintained at 30° C. The contractions were registered isometrically with a Statham-Force-transducer on a Grass-polygraph. The test compound was added to the organ bath so that the final concentration was $10^{-5}$ g/ml in each case. 5 auricles were used for each solution.

The following table gives the percentage decrease in the heart rate from an average of 5 auricles at a test compound concentration of $10^{-5}$ g/ml).

TABLE II

| Compound | Change in heart rate in % |
|---|---|
| A | −52 |
| B | −60 |
| D | −51 |
| E | −48 |

3. Acute toxicity:

The acute toxicity of the compounds in question was determined in mice (observation time: 14 days) after oral or intravenous application. The $LD_{50}$ was calculated from the percentage of animals which died after different doses within the observation time (see J. Pharmacol. exp. Therap. 96, 99 (1949)):

TABLE III

| Compound | $LD_{50}$ |
|---|---|
| A | 98 mg/kg i.v. |
| A | 1,570 mg/kg p.o. |
| B | 100 mg/kg i.v. |

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective heart rate reducing dosage unit of the compounds according to the present invention is from 0.33 to 5.0 mgm/kg body weight, preferably from 0.41 to 3.34 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 19

Tablets

The tablet composition is compounded from the following ingredients:

| | |
|---|---|
| 5,6-Dimethoxy-2N-(3-[α-(3,4-dimethoxy)-phenethyl-methylamino]-propyl)-phthalimidine hydrochloride | 100.0 parts |
| Lactose | 50.0 parts |
| Polyvinylpyrrolidone | 5.0 parts |
| Carboxymethyl cellulose | 19.0 parts |
| Magnesium stearate | 1.0 part |
| Total | 175.0 parts |

Preparation:

The phthalimidine compound and the lactose are intimately admixed with each other, the mixture is granulated with the aid of an aqueous solution of the polyvinylpyrrolidone, the granulate is dried, the dry granulate is admixed with the remaining ingredients, and the resulting composition is compressed into 175 mgm-tablets in a conventional tablet making machine. Each tablet contains 100 mgm of the phthalimidine compound and is an oral dosage unit composition with effective heart rate reducing action.

EXAMPLE 20

Coated pills

The pill core composition is compounded from the following ingredients:

| | |
|---|---|
| 5,6-Methylenedioxy-2N-(3-[α-(3,4-dimethoxy)-phenethyl-methylamino]-propyl)-phthalimidine hydrochloride | 50.0 parts |
| Corn starch, dry | 20.0 parts |
| Soluble starch | 2.0 parts |
| Carboxymethyl cellulose | 7.0 parts |
| Magnesium stearate | 1.0 part |
| Total | 80.0 parts |

Preparation:

The pill core composition is compounded in analogy to the tablet composition in the preceding example, and the composition is compressed into 80 mgm-pill cores which are subsequently coated with a thin shell consisting essentially of a mixture of talcum and gum arabic: Each coated pill contains 50 mgm of the phthalimidine compound and is an oral dosage unit composition with effective heart rate reducing action.

EXAMPLE 21

Rectal suppositories

The suppository composition is compounded from the following ingredients:

| | |
|---|---|
| 5,6-Dimethoxy-2-(3-[α-(3,4-dimethoxy)-phenethyl-methylamino]-propyl)-1,2-benzisothiazoline-1,1-dioxide hydrochloride | 150.0 parts |
| Suppository base (e.g. cocoa butter) | 1550.0 parts |
| Total | 1700.0 parts |

Preparation:

The suppository base is melted, the benzisothiazoline compound is homogeneously dispersed therein; and 1700 mgm-portions of the resulting mixture are poured into cooled suppository molds and allowed to harden therein. Each suppository contains 150 mgm of the benzisothiazoline compound and is a rectal dosage unit composition with effective heart rate reducing action.

EXAMPLE 22

Suspension

The suspension is compounded from the following ingredients:

| | |
|---|---|
| 5,6-Ethylenedioxy-2N-(3-[α-(3,4-methylenedioxy)-phenethyl-methylamino]-propyl)-phthalimidine hydrochloride | 5.0 parts |
| Carboxymethyl cellulose | 0.1 part |
| Methyl p-hydroxy-benzoate | 0.05 part |
| Propyl p-hydroxy-benzoate | 0.01 part |
| Sugar | 10.0 parts |
| Glycerin | 5.0 parts |
| Sorbitol solution, 70% | 20.0 parts |
| Flavoring | 0.3 part |
| Distilled water q.s.ad | 100.0 parts by vol. |

Preparation:

The distilled water is heated to 70° C, and the p-hydroxybenzoates as well as the glycerine and the carboxymethyl cellulose are dissolved therein. The solution is cooled to room temperature, and the phthalimidine compound is added while stirring. The solution is then made homogeneous. After addition of the sugar, the sorbitol solution and the flavoring, the resulting suspension is evacuated for de-aeration, while stirring.

5 ml of the suspension contain 250 mgm of the phthalimidine compound and are an oral dosage unit composition with effective heart rate reducing action.

Analogous results are obtained when any one of the other compounds embraced by formula I or a non-toxic, pharmacologically acceptable acid addition salt is substituted for the particular active ingredient in Examples 19 through 22. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula $$\begin{array}{c} R_2 \quad H \quad R_1 \\ \diagdown \diagup \diagdown \diagup \\ \diagup \diagdown \diagup \diagdown \quad N-(CH_2)_n-N-CH-CH_2- \\ SO_2 \quad \quad R_5 \\ R_3 \end{array} \begin{array}{c} R_6 \\ \diagdown \\ \diagup \\ R_7 \end{array}$$

wherein $R_1$ is hydrogen, lower alkyl or phenyl,
$R_2$ is hydrogen, chlorine or methoxy,
$R_3$ is hydrogen or methoxy
$R_2$ and $R_3$, together with each other, are methylenedioxy or ethylenedioxy,
$R_4$ and $R_5$ are each hydrogen or lower alkyl, $R_6$ is hydrogen or lower alkoxy, $R_7$ is lower alkoxy, $R_6$ and $R_7$, together with each other, are methylenedioxy or ethylenedioxy, and $n$ is 2 or 3, or a non-toxic, pharmacologically acceptable acid addition salt thereof.

2. A compound of claim 1, which is 5,6-dimethoxy-2-(3-[α-(3,4-dimethoxy)-phenylethyl-methylamino]-propyl)-1,2-benzisothiazoline-1,1-dioxide or a non-toxic, pharmacologically acceptable acid addition salt thereof.

3. A pharmaceutical dosage unit composition consisting essentially of an inert pharmaceutical carrier and an effective heart rate reducing amount of a compound of claim 1.

4. The method of reducing the heart rate in a warm-blooded animal in need of such treatment, which comprises perorally, parenterally or rectally administering to said animal an effective heart rate reducing amount of a compound of claim 1.

* * * * *